(12) United States Patent
Vedrine

(10) Patent No.: US 8,137,313 B2
(45) Date of Patent: Mar. 20, 2012

(54) DEVICE FOR INJECTION OF A PRODUCT, IN PARTICULAR FOR MEDICAL USE

(75) Inventor: Lionel Vedrine, Ridgewood, NJ (US)

(73) Assignee: Becton Dickinson France S.A.S. (FR)

( * ) Notice: Subject to any disclaimer, the term of this patent is extended or adjusted under 35 U.S.C. 154(b) by 531 days.

(21) Appl. No.: 10/573,226

(22) PCT Filed: Sep. 14, 2004

(86) PCT No.: PCT/FR2004/002330
§ 371 (c)(1),
(2), (4) Date: Nov. 20, 2008

(87) PCT Pub. No.: WO2005/030302
PCT Pub. Date: Apr. 7, 2005

(65) Prior Publication Data
US 2009/0069754 A1    Mar. 12, 2009

(30) Foreign Application Priority Data

Sep. 26, 2003 (FR) .................................. 03 11314

(51) Int. Cl.
*A61M 5/20* (2006.01)
(52) U.S. Cl. ......................... 604/135; 604/218
(58) Field of Classification Search .................. 604/131, 604/133–139
See application file for complete search history.

(56) References Cited

U.S. PATENT DOCUMENTS 2,752,918 A * 7/1956 Uytenbogaar ................ 604/136

FOREIGN PATENT DOCUMENTS

| EP | 0 516 473 A1 | 12/1992 |
| FR | 2 842 428 A1 | 1/2004 |
| WO | 01/07104 A1 | 2/2001 |

* cited by examiner

*Primary Examiner* — Kevin C Sirmons
*Assistant Examiner* — Brandy C Scott
(74) *Attorney, Agent, or Firm* — Hoffmann & Baron, LLP

(57) ABSTRACT

A medical device for the injection of a product. The device includes a body receiving an injection needle and a container containing the product to be injected; an arrangement for holding the needle in an injection position; an arrangement for holding the container in a position permitting injection; and, a piston engaged in the container. The device also includes first and second actuators which make it possible, at the end of the injection, to respectively release the arrangement for holding the needle before, or simultaneously to, the release of the arrangement for holding the container. A container support is mounted slidably on the body and is displaceable relative to the latter in order to perform the injection. The container support is held in a standby position before injection with the needle being held in the injection position.

4 Claims, 5 Drawing Sheets

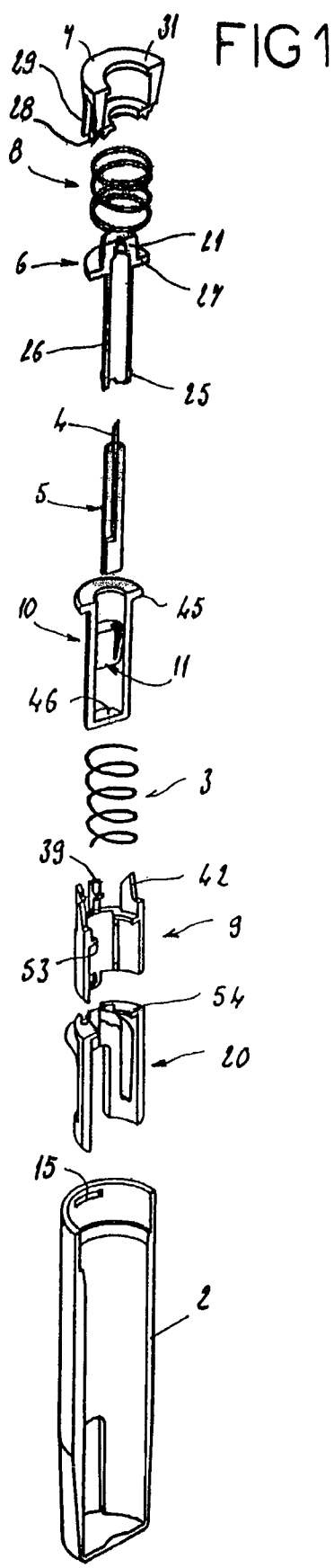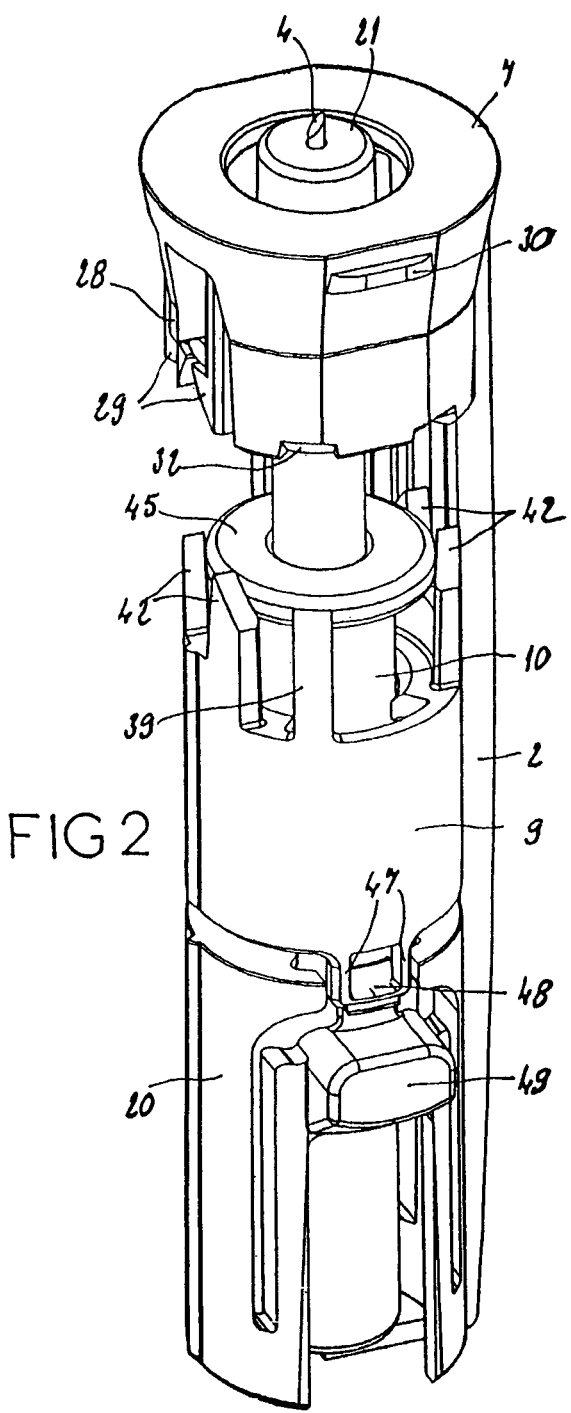

DEVICE FOR INJECTION OF A PRODUCT, IN PARTICULAR FOR MEDICAL USE

FIELD OF THE INVENTION

The present invention relates to a device for injection of a product, in particular for medical use. This device is intended in particular for allowing an intradermal injection to be performed.

BACKGROUND OF THE INVENTION

In the following description, the terms "proximal" and "distal" are considered with reference to the direction in which the product is injected.

It is customary to perform an intradermal injection using a traditional syringe, the needle being inserted at a direction forming a slight angle with the skin.

These traditional syringes do not guarantee complete reliability of the injection, nor complete safety against the risk of accidental needlestick injuries which can occur after the injection.

In order to reduce these risks to a minimum, it is important to limit the freedom of action of the end user of such injection devices.

The invention aims to overcome this fundamental problem.

The object of the invention is therefore to make available a device which guarantees complete reliability of the injection and complete safety against the risk of accidental needlestick injuries, by means of limiting the actions of the end user to a minimum.

SUMMARY OF THE INVENTION

The present invention concerns a device for injection of a product, in particular for medical use, comprising:
- a body receiving a hollow injection needle and a container containing the product to be injected, the needle and container being movable relative to said body between an injection position and a retracted position;
- means for holding the needle in position, which means normally hold the needle in said injection position, and which means can be released to permit movement of the needle to said retracted position;
- means for holding the container in position, which means normally hold the container in a position permitting injection, and which means can be released to permit movement of the container to said retracted position;
- a piston engaged in the container,
characterized in that it additionally comprises:
- first actuating means of means for holding the needle in position,
- second actuating means of means for holding the container in position,
- said first and second actuating means making it possible, at the end of the injection, to respectively release the means for holding the needle in position before the release of the means for holding the container in position, or to simultaneously release the means for holding the needle in position and the means for holding the container in position,
- a container support which is mounted slidably on the body and is displaceable relative to the latter in order to perform the injection, said container being connected to this support and being able to move relative to the latter between a position permitting injection and a retracted position,
- means for holding the container support in position, which means normally hold the container support in a standby position before the injection and can be released to permit displacement of the container support and to permit injection,
- means activating the release of the means for holding the container support permitting injection in position.

Before injection, the support is held in a fixed standby position relative to the body. The container is thus connected to the support. The user acts on the means activating the release of the means for holding the support in position. The displacement of the support relative to the body in the distal direction causes the displacement of the container in the same direction. As the needle is also held relative to the body in the injection position, the movement of the container generates a force on the piston which applies a pressure on the liquid. This pressure pushes the liquid contained in the container towards the needle and the patient's skin.

The first actuating means are separate from the second actuating means. Thus, at the end of the injection, said first actuating means cause the release of said means for holding the needle in position whereas, either simultaneously or subsequently, the second actuating means cause the release of said means for holding the container in position, thus making it possible to bring the needle and the container into the retracted position. This retraction guarantees complete safety against the risk of accidental needlestick injuries.

In particular, when the second actuating means cause the release of said means for holding the container in position subsequently to the release of said means for holding the needle in position by the first actuating means, then the chance to retract the needle before the full dose is administered (leakage, misdose, etc. . . ) is reduced.

Advantageously, the means for holding the support in position comprise:
- a ring mounted in a fixed manner inside the body and in the proximal part of the latter, this ring having at least one transverse tooth at its distal end,
- at least one hook situated at the proximal end of the support and intended to clip into said tooth,
- a spring whose distal end bears on a transverse internal step at the distal end of the support, and whose proximal end bears on a transverse wall situated at the distal end of the ring, said spring being in the compressed state when the tooth is clipped into the hook.

Advantageously, the means activating the release of the means for holding the support in position are in the form of a button integral with the tooth of the ring, said button protruding outside the body through a slot formed in the body for this purpose.

Thus, when the end user presses the button, the tooth, which is integral with the button, is deflected in the radial direction towards the axis of the device and frees itself from the hook of the support. As the support is no longer retained on the ring, the spring relaxes, carrying with it the support which moves in the distal direction. As the support is also connected to the container, it carries the latter in the distal direction and permits the injection.

The device according to the invention has the advantage of requiring only a minimal intervention on the part of the end user. The latter only has to press the button of the ring in order to carry out the injection.

Advantageously, the device comprises spring means which, at the end of the injection, bring the needle and the container into the retracted position without any external voluntary intervention.

According to a possible embodiment of the invention, said means for holding the needle in position comprise:
- a needle-supporting component comprising at least one locking means;
- at least one tab comprising a locking means able to cooperate with that of said needle-supporting component, this tab being movable radially between a normal, radially inward position, in which said locking means engage so as to hold said needle-supporting component in position relative to said body, and a radially outward position in which a zone of the support moves this tab radially outwards in such a way as to free said lock, which thus frees said needle-supporting component relative to said body.

According to a possible embodiment of the invention, said means for holding the container in position comprise:
- a flange formed at that end of the container remote from the closed end of this container;
- engagement means integral with said support and allowing said flange to be connected to the support; and
- at least one tab comprising said engagement means and able to move in the radial direction of this support, between a radially inward position, in which said engagement means connect said flange to the support, and a radially outward position in which said engagement means are withdrawn radially from this flange, thereby releasing it.

The piston engaged in the container is preferably designed in such a way that, in a first configuration of the piston or relative position of this piston and of this container, it closes the container so as to isolate the product from the outside of this container, and, in a second configuration of the piston or relative position of this piston and of this container, it permits the passage of the product to outside the container. The piston can in particular comprise at least one peripheral zone which, in said first configuration of the piston, is able to bear tightly against the wall of the container, and, in said second configuration of the piston, is able to withdraw under the pressure of the product to be injected, thereby permitting passage of this product.

The piston can also comprise a pierceable zone opposite the proximal end of the needle. The displacement of the container relative to the needle then causes the proximal end of the needle to pierce this pierceable zone of the piston until it comes into communication with the product to be injected and to permit this product to flow through the needle.

The attached figures illustrate, by way of example, a preferred embodiment of the device according to the invention.

BRIEF DESCRIPTION OF THE FIGURES

FIG. 1 is an exploded perspective view in a cross section passing along its axis;

FIG. 2 is a perspective view in the assembled state;

DETAILED DESCRIPTION

Figure 5:
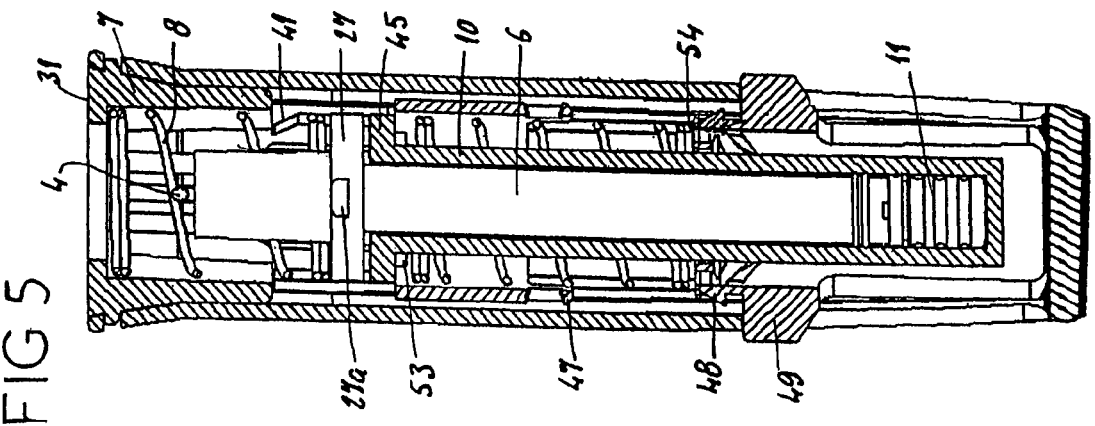
FIGS. 3 to 5 are cross-sectional views of the device according to the invention, in the storage position, end-of-injection position, and retracted position, respectively.

The figures show a device 1 for injection of a product, in particular for medical use.

As is shown more particularly in FIGS. 1 and 2, the device 1 comprises a body 2, a hollow injection needle 4, an injection-activating spring 3, components 5 to 7 for mounting the needle 4, a spring 8 for the retraction movement, a container support 9, a container 10, a piston 11, and a ring 20, all described in detail below.

The body 2 is of a generally tubular shape and comprises a circular rib 15 at its distal end.

The needle 4 is fixed to the component 5. The latter is of a generally cylindrical solid shape and has a groove and a hole which form a flow conduit communicating with the cavity of the needle 4.

The component 6 has a tube-shaped proximal part 26 in which the component 5 is tightly received, and it comprises a distal hole to allow the needle 4 to be engaged through a boss 21. The distal face of the boss 21 forms a surface by which the device 1 engages on the patient's skin. In the injection position, the needle 4 preferably extends by a distance of 0.5 mm to 3 mm beyond the surface with which the device 1 engages on the patient's skin. The part 26 is intended to be introduced into the container 10, as has been mentioned above, and comprises a seal 25 at its proximal end. This part 26 thus makes it possible to displace the piston 11 inside the container 10 when the support 9 is displaced relative to the body 2, as will be seen later.

The component 6 also comprises a flange 27 which can be clipped, by means of a lug 27a, into openings provided on four tabs 29 integral with the component 7, said tabs 29 being arranged in pairs opposite a wall 28 which extends in the proximal direction from the distal end of the component 7, said tabs 29 being able to deflect circumferentially.

The component 7 is intended to be inserted tightly into the distal opening of the body 2, and a distal flange 30 which it comprises is positioned in the distal recess delimited by the rib 15. This tight engagement permits securing of the component 7 to the body 2.

The component 7 also comprises an opening delimited by a shoulder 31 whose diameter is smaller than the diameter of the spring 8 for initiating retraction.

Figure 3:
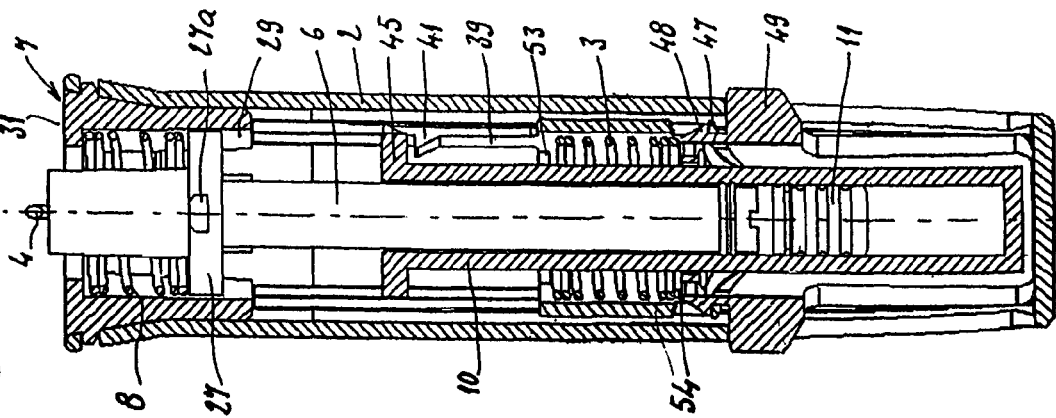

As is shown in FIG. 3, this shoulder 31 allows the spring 8 to be maintained in the compressed state between the proximal face of this shoulder 31 and the distal face of the flange 27 when the component 6 is clipped into the component 7.

The component 7 also comprises, at its proximal end, two bevels 32 forming ramps. It will be seen from FIG. 2 that the tabs 29 have internal inclined ramps formed in their proximal parts.

The support 9 is engaged in the body 2 and is able to slide relative to the latter.

At its distal end, the support 9 forms two radially movable tabs 39 which. are provided with internal projections 41 (see FIG. 3) forming stops for receiving a flange 45 which the container 10 comprises. This abutment of the flange 45 against the projections 41 makes it possible to connect the flange 45 to the support 9 in the direction of displacement of the support 9, thereby permitting injection.

The support 9 also forms four walls 42 situated between the tabs 39. As is shown in FIGS. 1 to 3, the tabs 39 comprise, at their distal ends, internal inclined ramps which are able to cooperate with the ramps of the bevels 32 at the end of the injection stroke, and the walls 42 comprise, at their distal ends, external inclined ramps which are able to cooperate with the internal ramps of the tabs 29, likewise at the end of the injection stroke.

Figure 13:
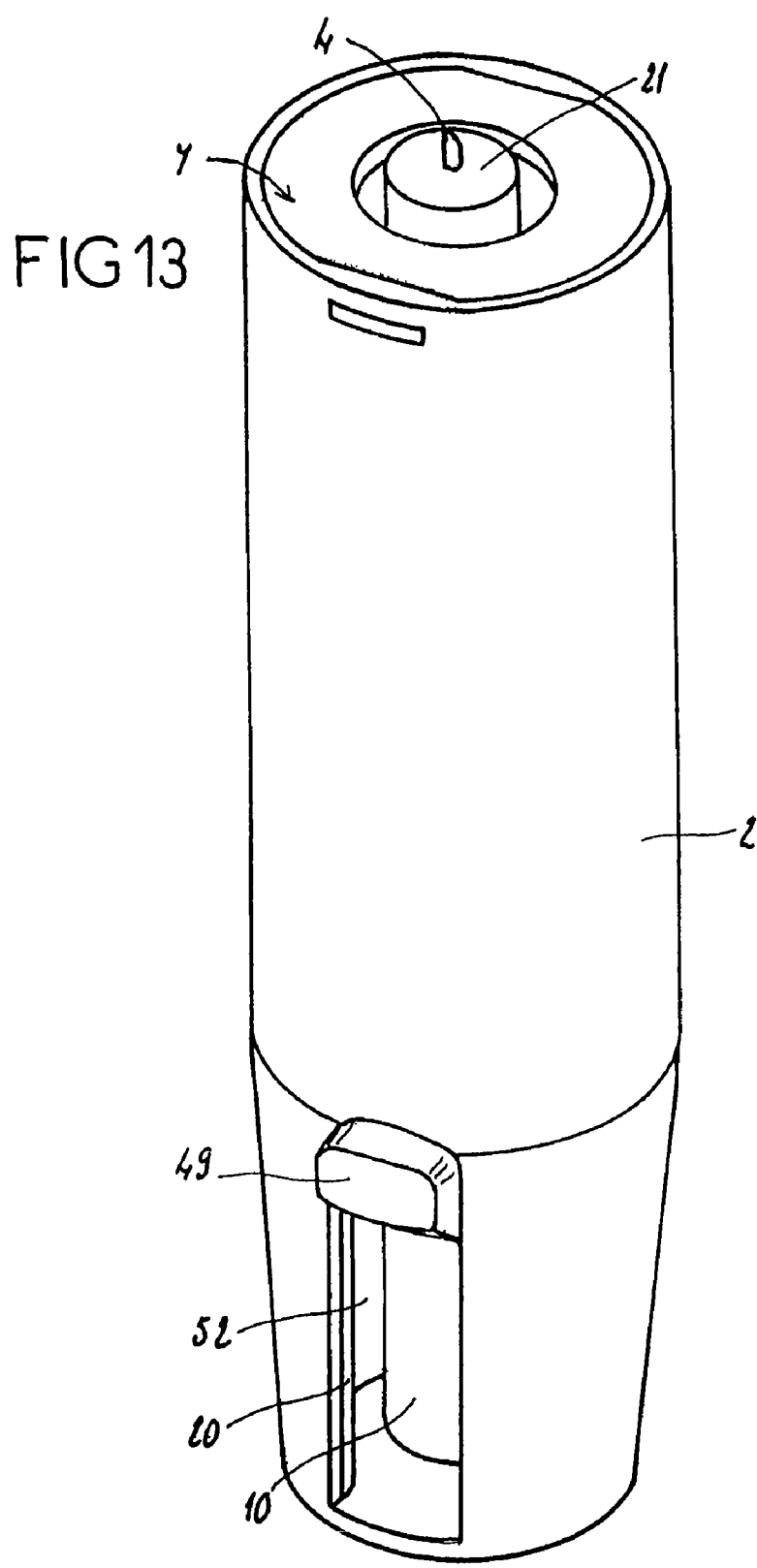
FIG. 13 is a perspective view of the device according to the invention.

At its proximal end, the support 9 comprises at least one hook 47 intended to clip together with a transverse tooth 48 situated on the distal end of the ring 20. This ring 20 is mounted in a fixed manner inside the body 2 in the proximal part of the latter. The ring 20 also comprises, on its outer face, at least one button 49 which is integral with the tooth 48 and which protrudes outside the body 2 through a slot 52 formed in the body 2 for this purpose, as is shown in FIG. 13.

An injection-activating spring 3 is arranged between the support 9 and the ring 20. As is shown in FIG. 3, the distal end of this spring 3 bears on a transverse inner step 53 at the distal end of the support 9 and its proximal end bears on a transverse wall 54 situated at the distal end of the ring 20. The injection-activating spring 3 is in the compressed state when the tooth 48 is clipped into the hook 47, as is shown in FIG. 3.

At the opposite end from the flange 45, the container 10 comprises a bottom 46. The product to be injected is contained between the piston 11 and the walls of the container 10.

Figure 6:
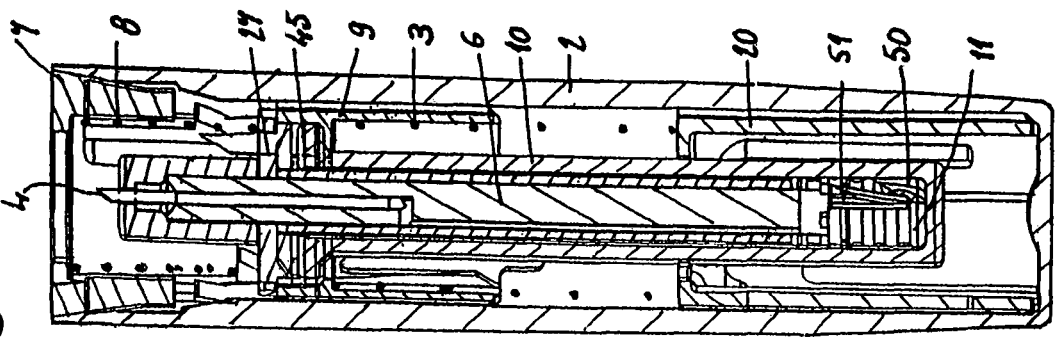
FIG. 6 is a cross-sectional view, along the line XX in FIG. 3, of the device in the storage position.

The piston 11 is made of a flexible material, especially an elastomer. It is of a conical shape and is placed in the container 10 in such a way that its face having a smaller surface area is directed towards the product to be injected. In this way, as is shown in FIG. 6, it forms a gap 50 between itself and the wall of the container 11. Moreover, the piston 11 comprises a lateral blind hole 51 extending a large part of the way through its thickness, from its distal axial face, next to the side wall of the piston 11 which delimits said gap 50. The hole 51 is of such a shape that it follows this side wall, at least approximately, and thus delimits a peripheral zone extending over part of the periphery of the piston 11.

Figure 7:
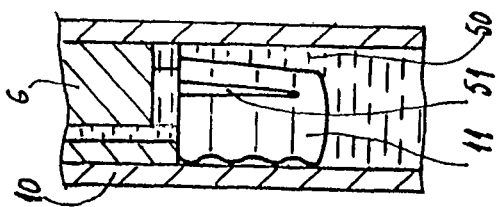
FIG. 7 is a partial cross-sectional view of the position of the piston in the injection phase.

As a comparison of FIGS. 6 and 7 shows, this peripheral zone normally adopts a radially outward position shown in FIG. 6, in which it bears tightly against the wall of the container 10, and can assume a radially inward position shown in FIG. 7, into which it withdraws, under the pressure of the product to be injected, as the latter passes between the piston 11 and the container 10, due to the piston 11 bearing against the product.

Figure 10:
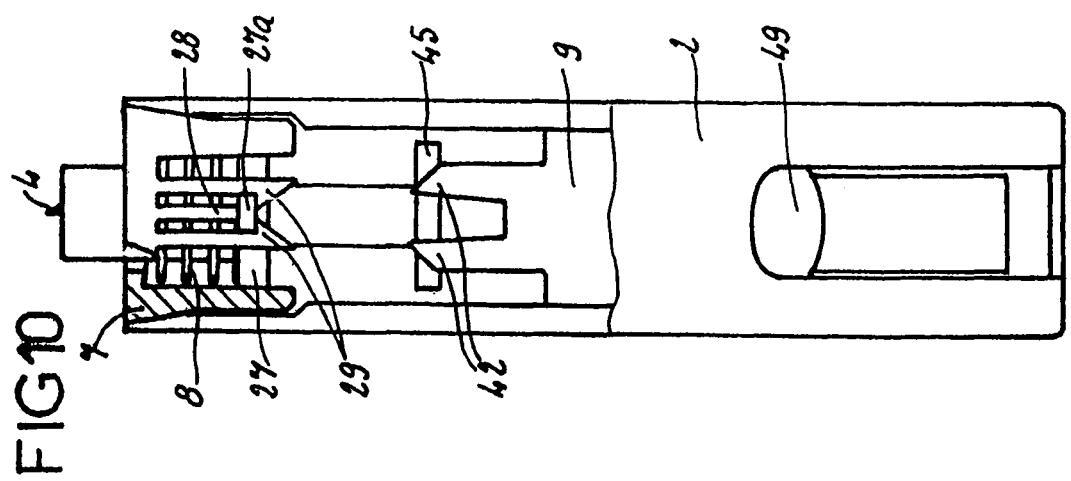
FIGS. 10 to 12 are simplified side views of the device in the storage position, end-of-injection position and retracted position, respectively, showing the release of the means for holding the needle in position.

In practice, the device 1 is initially in the storage position shown in FIGS. 3, 6 and 10, in which the lug 27a of the flange 27 is in engagement with the tabs 29 and the flange 45 is kept in position by the projections 41. In this position, the needle 4 projects beyond the distal end of the device according to the depth desired for injection, which is an intradermal injection in the example shown. In this position too, the tooth 48 is clipped into the hook 47 and the injection-activating spring 3 is in the compressed state.

The end user presses the button or buttons 49 projecting from the body 2 through the slot 52. As the button 49 is integral with the tooth 48, the latter deflects radially towards the axis of the device under the pressure exerted on the button 49. The tooth 48 is then freed from the hook 47 and the injection-activating spring 3 relaxes, carrying the support 9 with it in the distal direction. As the support 9 is connected to the container 10 on account of the flange 45 of the container 10 being held by the tabs 39 of the support 9, the container 10 is likewise moved in the distal direction.

The displacement of the container 10 with the support 9 presses the piston 11 against the injectable product, which causes the product to flow between the piston 11 and the container 10, as is shown in FIG. 7.

Figure 4:
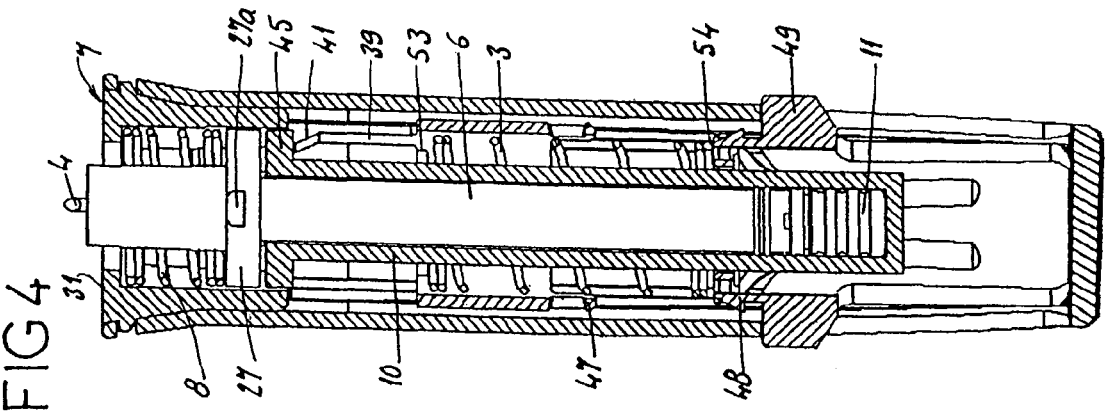
Figure 8:
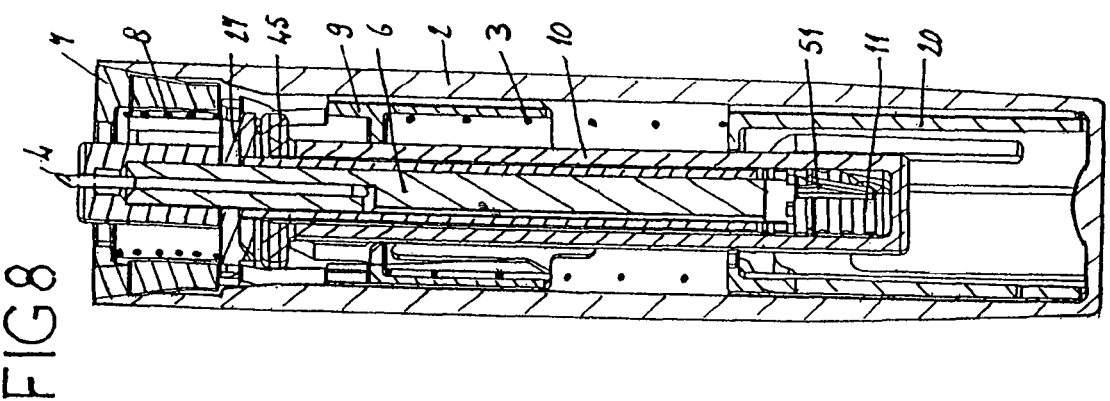
FIGS. 8 and 9 are cross-sectional views, along the line XX in FIG. 3, of the device in the end-of-injection position and retracted position, respectively.
Figure 9:
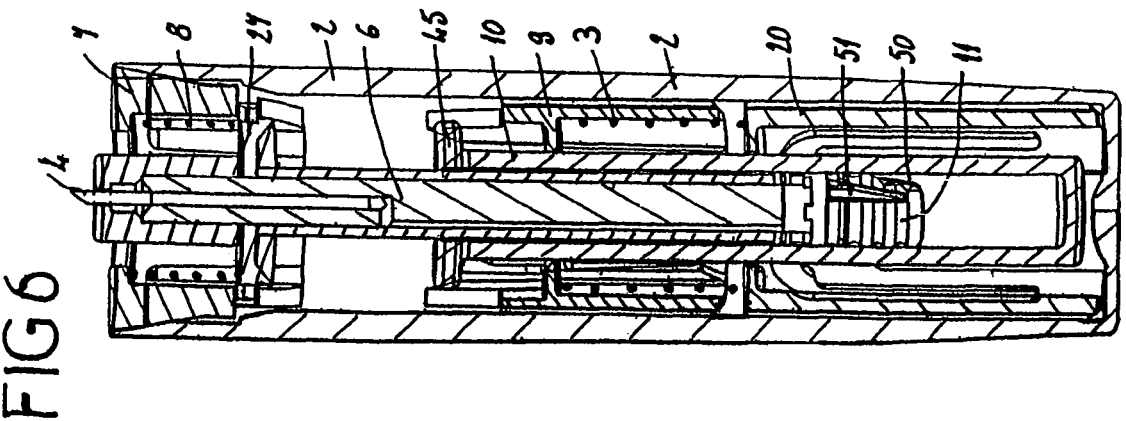
Figure 11:
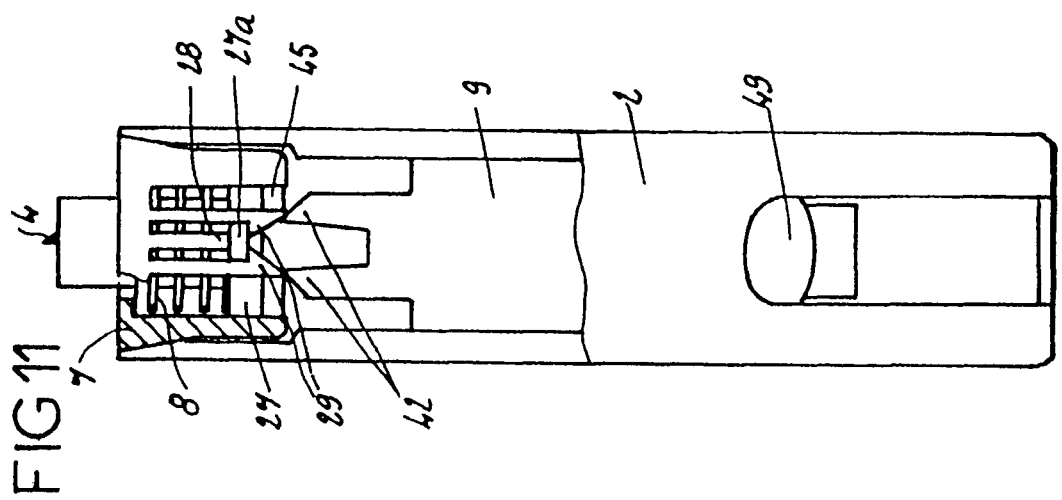
Figure 12:
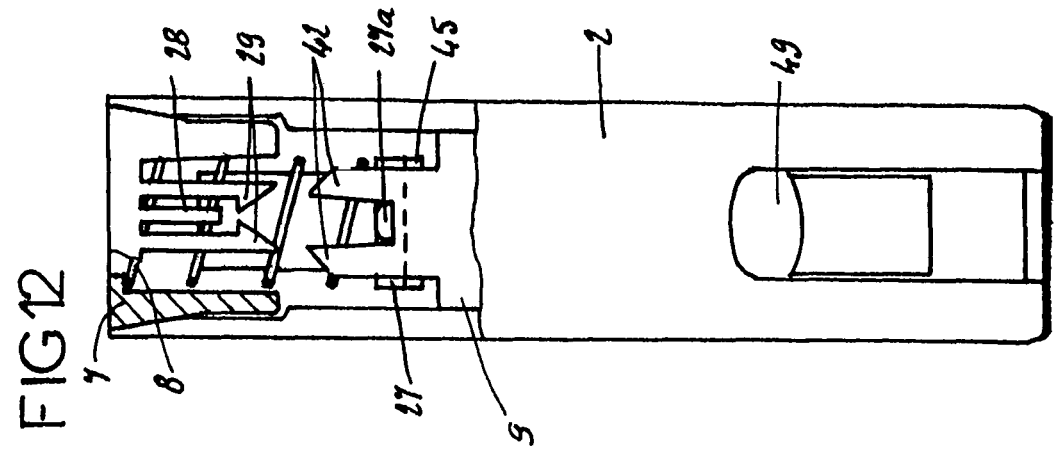

As is shown in FIGS. 4, 8 and 11, on approaching the end-of-injection position the ramps of the tabs 39 and of the walls 42 come to bear against, respectively, the ramps of the bevels 32 and of the tabs 29, such that the tabs 29 are deflected circumferentially and the tabs 39 are moved towards radially outward positions, in which positions the tabs 29 and 39 free, respectively, the lug 27a of the flange 27 and the flange 45. The retraction-activating spring 8 can then relax, which causes simultaneous retreat of the components 5 and 6, and hence of the needle 4, and also of the container 10 on account of the friction of the seal 25, towards a retracted position shown in FIGS. 5, 9 and 12. In this position, the distal end of the needle 4 is situated back from the distal face of the component 7 and the flange 45 is situated back from the projections 41 at the proximal end.

It will be evident from the above that the invention affords a number of crucial improvements to the corresponding devices of the prior art, requiring of the end user only a minimal intervention for performing injection and for retracting the needle, thus making the device completely safe against the risk of accidental needlestick injuries which can occur after injection.

It goes without saying that the invention is not limited to the embodiment described above by way of example, but that instead it encompasses all alternative embodiments coming within the scope of protection defined by the attached claims. In particular, the piston can comprise a pierceable zone located opposite the proximal end of the needle, this proximal end projecting from the proximal end of the component 5 in which it is held.

The invention claimed is:

1. Device (1) for injection of a product, in particular for medical use, comprising:
   a body (2) receiving a hollow injection needle (4) and a container (10) containing the product to be injected; the needle (4) and container (10) being movable relative to said body between an injection position and a retracted position;
   means (5 to 7; 28, 29) for holding the needle in position, which means normally hold the needle (4) in said injection position, and which means can be released to permit movement of the needle (4) to said retracted position;
   means (39, 41, 45) for holding the container (10) in position, which means normally hold the container (10) in a position permitting injection, and which means can be released to permit movement of the container (10) to said retracted position;
   a piston (11) engaged in the container (10),
   characterized in that it additionally comprises:
   first actuating means (42) of means (5 to 7; 28, 29) for holding the needle (4) in the injection position,
   second actuating means (32) of means (39, 41, 45) for holding the container (10) in position,
   said first and second actuating means (42, 32) making it possible, at the end of the injection, to respectively release the means (5 to 7; 28, 29) for holding the needle (4) in the injection position before the release of the means (39, 41, 45) for holding the container (10) in position, or to simultaneously release the means (5 to 7; 28, 29) for holding the needle (4) in position and the means (39, 41, 45) for holding the container (10) in position,
   a container support (9) which is mounted slidably on the body (2) and is displaceable relative to the latter in order to perform the injection, said container (10) being connected to this support (9) and being able to move relative to the latter between a position permitting injection and a retracted position, means (3, 47, 48) for holding the container support (9) in position, which means normally hold the container support (9) in a standby position before the injection and can be released in order to permit displacement of the container support (9) and to permit injection, means (49) actuating the release of the means (3, 20, 47, 48) for holding the container support (9) permitting injection in position, wherein, said means (5 to 7; 28,29) for holding the needle (4) holds the needle (4) in the injection position with the container support (9) in the stanby position before the injection.

2. Device (1) according to claim 1, characterized in that the means (3, 20, 47, 48) for holding the support in position comprise:

a ring (20) mounted in a fixed manner inside the body (2) and in the proximal part of the latter, this ring (20) having at least one transverse tooth (48) at its distal end, at least one hook (47) situated at the proximal end of the support (9) and intended to clip into said tooth (48), an injection-activating spring (3) whose distal end bears on a transverse internal step (53) at the distal end of the support (9), and whose proximal end bears on a transverse wall (54) situated at the distal end of the ring (20), said spring (3) being in the compressed state when the tooth (48) is clipped into the hook (47).

3. Device (1) according to claim 2, characterized in that the means (49) activating the release of the means for holding the support (9) in position are in the form of a button (49) integral with the tooth (48) of the ring (20), said button (49) protruding outside the body (2) through a slot (52) formed in the body (2) for this purpose.

4. Device (1) according to any one of the preceding claims, characterized in that, in the injection position, the needle (4) extends by a distance of 0.5 mm to 3 mm beyond a surface with which the device (1) engages on the patient's skin.

* * * * *